(12) United States Patent
Kormann et al.

(10) Patent No.: US 7,169,040 B2
(45) Date of Patent: Jan. 30, 2007

(54) CROP MEASURING ARRANGEMENT

(75) Inventors: Georg Kormann, Homburg (DE); Werner Flohr, Kaiserslautern-Dansenberg (DE)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 10/940,831

(22) Filed: Sep. 14, 2004

(65) Prior Publication Data

US 2005/0085283 A1 Apr. 21, 2005

(30) Foreign Application Priority Data

Oct. 15, 2003 (DE) ................ 103 48 040

(51) Int. Cl.
*A01F 12/16* (2006.01)
*A01F 21/00* (2006.01)
*A01D 75/18* (2006.01)

(52) U.S. Cl. ..................... 460/7; 250/339.11
(58) Field of Classification Search ............ 460/7, 460/4, 6; 56/10.2 R; 356/328, 402–411; 250/339.11, 339.12, 226

See application file for complete search history.

(56) References Cited

U.S. PATENT DOCUMENTS

| | | | |
|---|---|---|---|
| 5,132,538 A * | 7/1992 | Norris ................... 250/339.09 |
| 5,324,979 A * | 6/1994 | Rosenthal ............... 250/504 R |
| 5,327,708 A | 7/1994 | Gerrish | |
| 5,991,025 A * | 11/1999 | Wright et al. ............... 356/328 |
| 6,100,526 A * | 8/2000 | Mayes ................... 250/339.11 |
| 6,421,990 B1 | 7/2002 | Ohlemeyer et al. | |
| 6,559,655 B1 | 5/2003 | Rosenthal et al. | |
| 6,624,888 B1 | 9/2003 | Panigrahi et al. | |
| 6,791,683 B1* | 9/2004 | Sjodin ........................ 356/326 |
| 6,845,325 B1* | 1/2005 | Valero et al. ................. 702/14 |
| 2001/0000910 A1 | 5/2001 | Rosenthal et al. | |
| 2003/0063276 A1 | 4/2003 | Sjodin et al. | |

FOREIGN PATENT DOCUMENTS

| | | |
|---|---|---|
| DE | 102 36 515 | 8/2002 |
| EP | 0 511 184 | 4/1992 |
| EP | 0 843 959 | 5/1998 |
| EP | 1 053 671 | 3/2000 |

* cited by examiner

*Primary Examiner*—Árpád Fábián Kovács

(57) ABSTRACT

A crop measuring arrangement is arranged on a harvesting vehicle to interact with a material that is to be investigated in order to detect at least one component of the material, and that can be fastened to a vehicle by means of a retaining arrangement, so that the measuring arrangement can be operated in the condition in which it is fastened to the retaining arrangement in order to analyze material handled and/or processed by means of the vehicle. The retaining arrangement for securing the measuring arrangement to the vehicle is constructed so that the measuring arrangement can be easily separated from the retaining arrangement and used to investigate material in a stationary application.

6 Claims, 3 Drawing Sheets

CROP MEASURING ARRANGEMENT

FIELD OF THE INVENTION

The invention concerns a measuring arrangement that is arranged to interact with a material that is to be investigated in order to detect at least one component contained in the material, and that can be fastened to a vehicle by means of a retaining arrangement, so that the measuring arrangement can be operated in the condition in which it is fastened to the retaining arrangement in order to analyze material handled and/or processed on the part of the vehicle.

BACKGROUND OF THE INVENTION

U.S. Pat. No. 6,421,990 proposes a measuring arrangement that is attached to an agricultural machine. The harvested crop flows past the measuring arrangement and is investigated by the measuring arrangement in regard to certain characteristics such as moisture, or the contents of certain organic components. It is proposed that the measuring arrangement be attached within the machine or to a slide outside of the machine. The sensor described is used exclusively on the harvesting machine.

Furthermore similar measuring arrangements are known, that are applied in a stationary arrangement, for example, in order to analyze food samples (see EP 0 511 184 A).

For the analysis of components of organic material, appropriate measuring arrangements as a rule include sensors that operate in the range of wave lengths of the near infra-red (NIR), they are equipped with light sources and analyzers. Sensors of this type are relatively costly and expensive. In applications in which organic materials are to be analyzed both during the harvest as well as in a stationary applications, the acquisition of two sensors has been shown to be required.

The problem underlying the invention is seen in the need to avoid the disadvantages described above.

SUMMARY OF THE INVENTION

According to the present invention, there is provided an improved crop measuring arrangement for use with a crop harvester.

It is proposed that the measuring arrangement be configured so that it can be removed from the vehicle and used separately from the vehicle.

In this way the measuring arrangement can be used on the vehicle, on the one hand, in order to analyze material conveyed or processed by the latter, on the other hand it can also be removed from the vehicle and used for a stationary analysis of other materials. Thereby this measuring arrangement can be applied to every type of vehicle (for example, wood harvesting machines, wood processing vehicle, self-propelled, attached or towed harvesting machines, such as combines, forage harvesters or balers, forage mixing vehicles, sowing machines, manure distributing systems, as well as stationary applications, for example, in the office, on a vehicle weighing scale, cereal crop take-up arrangements or elevator installations, or for the analysis of daily feed rations, or in an automobile or a truck for mobile quality control. An advantage lies in the fact that the measuring arrangement can be applied in extensive applications within one business, particularly an agricultural business. Thereby the time period for the application of the measuring arrangement is extended from a few weeks of the harvest to the entire year.

The analysis of materials can be performed, for example, by an optical sensor. As a rule such sensors operate in the near infra-red region. The measuring arrangement can operate in transmission and/or reflection mode and/or in any desired other wave length region.

The measuring arrangement is fastened to a retaining arrangement on the vehicle, that makes it possible to bring the material that is to be investigated into an area in which it can be analyzed by the measuring arrangement; hence an arrangement for the presentation of the sample is available. When it is in a condition in which it is separate from the vehicle, the measuring arrangement could be used without any additional retaining arrangement and could, for example, be held manually in a position in which it interacts with the material that is to be investigated. If, however, a second retaining arrangement is used there for the measuring arrangement as well, this arrangement is appropriately equipped with an arrangement for the presentation of the sample. During the measurement, the sample may be in either a resting or a moving condition.

BRIEF DESCRIPTION OF THE DRAWINGS

The drawing shows an embodiment of the invention that shall be described in greater detail in the following.

DESCRIPTION OF THE PREFERRED EMBODIMENTS

Figure 2:
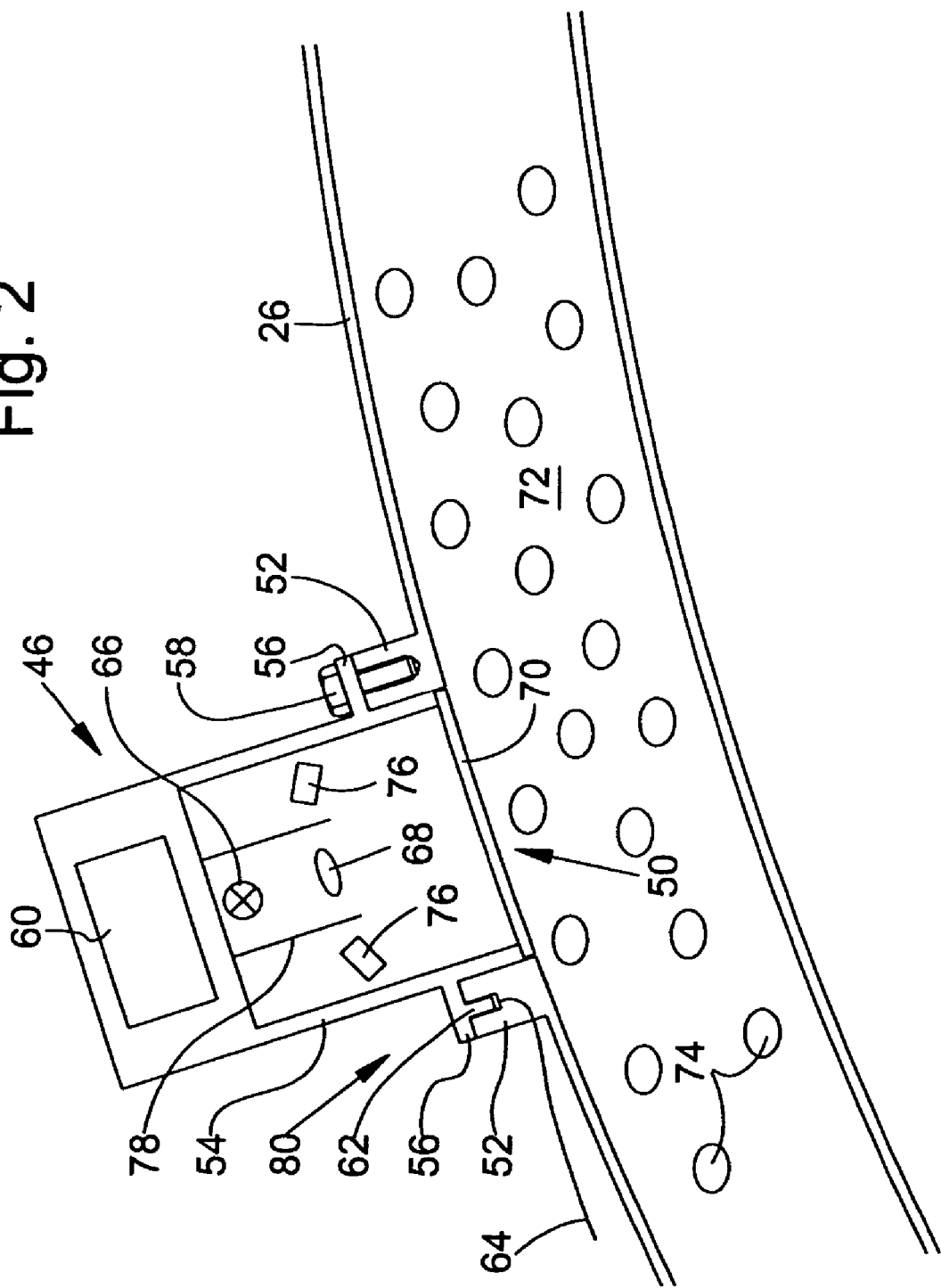
FIG. 2 is an enlarged cross section of the measuring arrangement fastened to a crop delivery duct of the harvesting machine.
Figure 3:
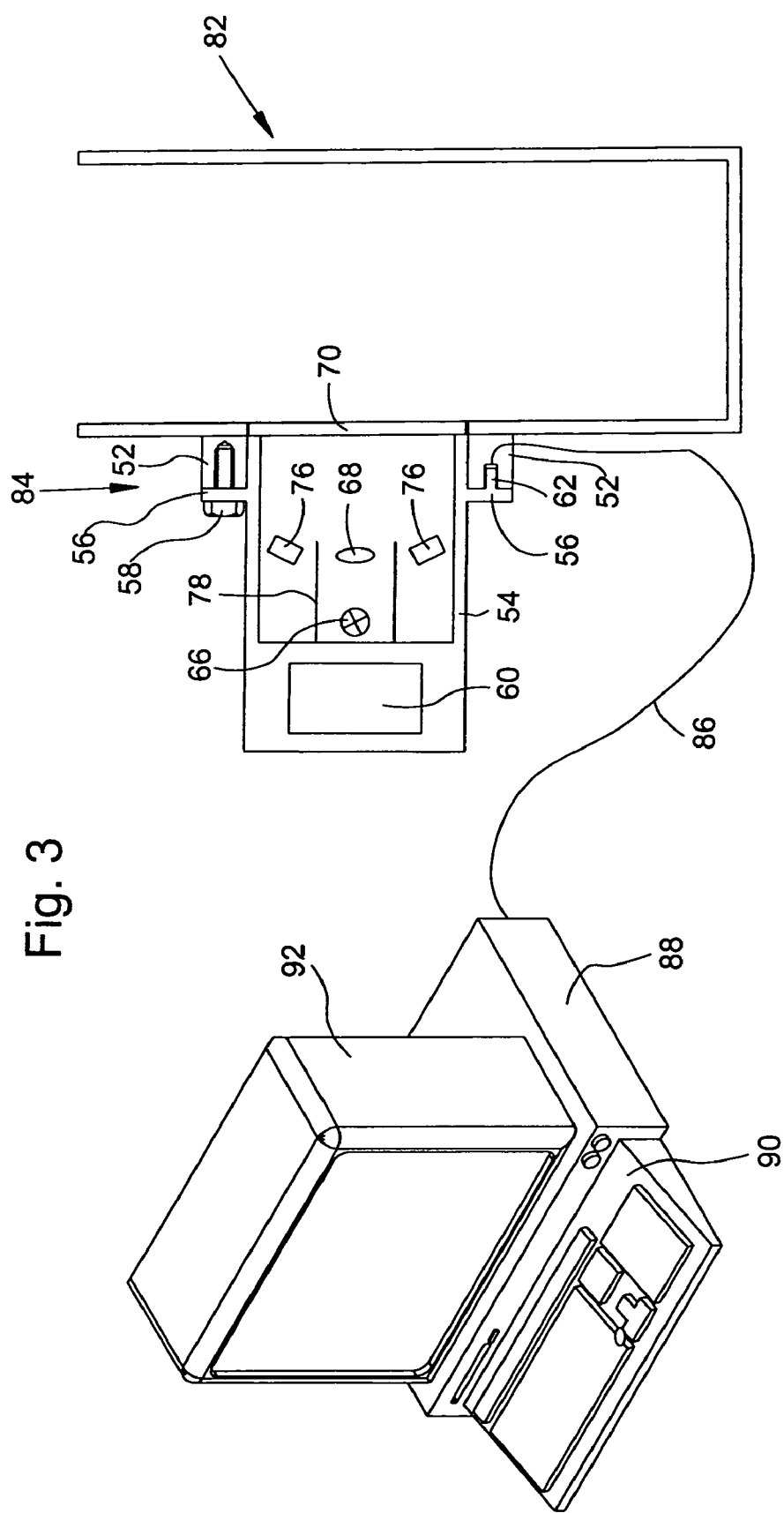
FIG. 3 is a view showing the measuring arrangement with a second retaining arrangement and a computer for the evaluation of the measurement results.

The embodiment shown is applied to a harvesting machine 10 (FIGS. 1 and 2) and, alternatively, to a stationary measurement container (FIG. 3). The harvesting machine 10, shown in FIG. 1 in the form of a self-propelled forage harvester, is supported on a frame 12 that is carried by front and rear wheels 14 and 16. The harvesting machine 10 is controlled from an operator's cab 18 from which a harvested crop take-up arrangement 20 can be viewed. Crop, such as corn, grass or the like, taken up from the ground by the take-up arrangement 20 is conducted to a chopper drum 22 which chops the crop into small pieces and delivers it to a conveying arrangement 24. The crop leaves the harvesting machine 10 through a discharge duct 26 to an accompanying trailer. A post-chopper reduction arrangement 28 is mounted between the chopper drum 22 and the conveying arrangement 24, and conducts the crop to be conveyed tangentially to the conveying arrangement 24.

Figure 1:
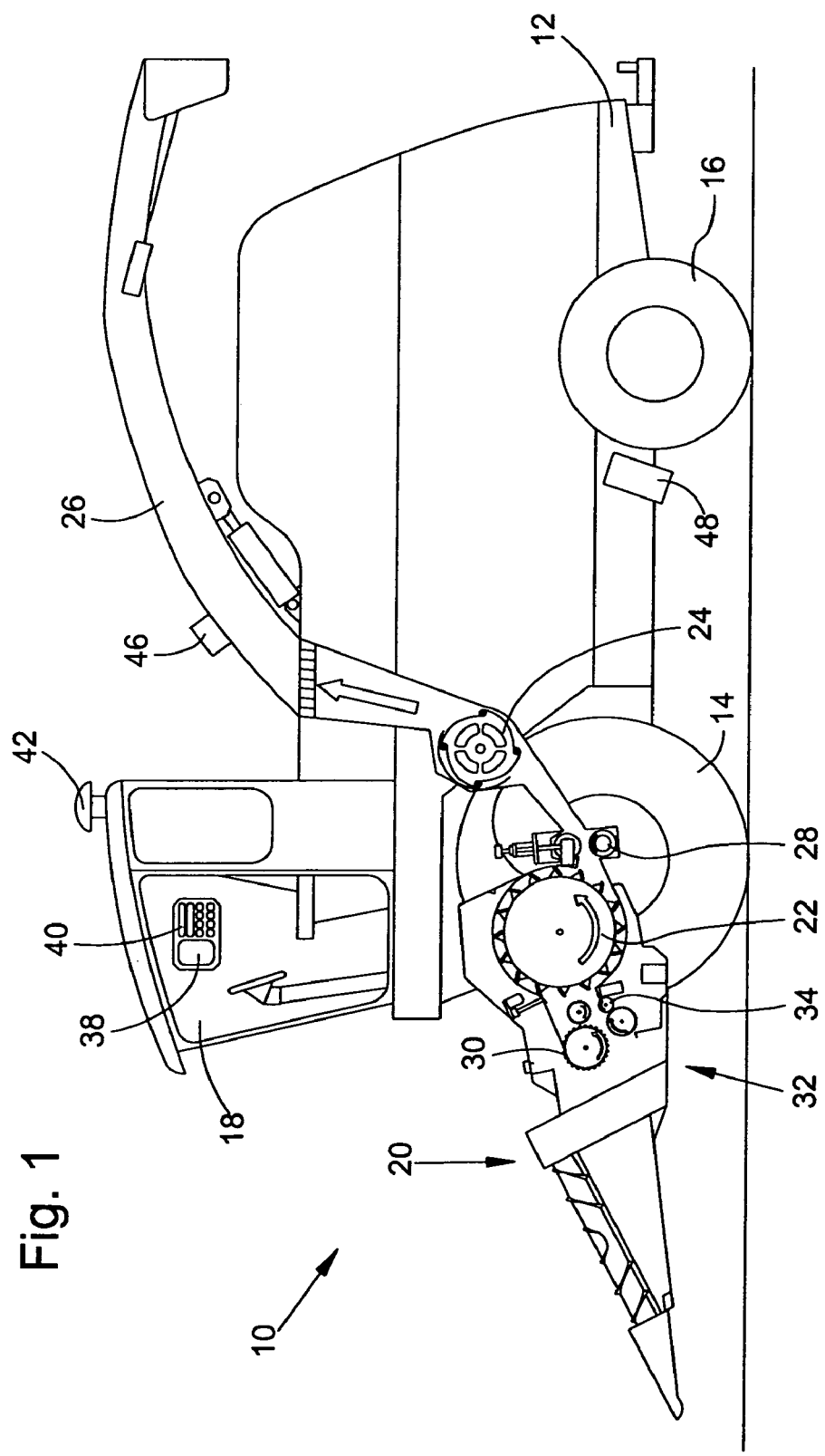
FIG. 1 is a schematic left side view of a harvesting machine equipped with a measuring arrangement.

Several sensors are provided on the harvesting machine 10 shown in FIG. 1, for the measurement of the harvested crop flowing through the harvesting machine 10 per unit of time, the so-called throughput. A first throughput sensor 30 measures the spacing between two rough pressing rolls 32 that are arranged between the harvested crop take-up arrangement 20 and the chopper drum 22, between which the harvested crop is conveyed, using a linear or rotary resistance (potentiometer) actuated by the spring-loaded rough pressing rolls 32. Moreover the rotational speed of one of the rough pressing rolls 32 is measured by means of a second sensor 34. In addition sensors can measure the drive torque of the conveying arrangement 24 as well as that of the post-chopper reduction arrangement 28.

An on-board computer 40 connected to a display arrangement 38 is used to record and evaluate the data measured.

In order to calculate a yield, additional data are required for the actual forward propulsion velocity and the width of operation. The forward propulsion velocity can be derived from data of the forward propulsion arrangements of the harvesting machine 10 or detected by a radar sensor 48. By using a global positioning sensor (GPS) 42 for the detection of the actual position, the yield can be mapped specific to partial areas by means of the on-board computer 40.

According to the invention, a measuring arrangement 46 is provided for the measurement of certain components contained in the harvested crop. It determines the percentage of these components in the harvested crop and operates optically in a reflection mode in the visual range and/or the near infra-red range. Thereby moisture, raw protein, fat contents etc. of the harvested crop can be determined, geo-referenced, stored in memory and displayed by the display arrangement 38. Moreover, the measuring arrangement 46 is arranged to detect further parameters of the harvested crop, particularly the fiber length, the fiber content and the contents of solid matter.

The attachment of the measuring arrangement 46 to the discharge duct 26 is shown in greater detail in FIG. 2. The flat wall of the discharge duct 26 extending transverse to the direction of operation is provided on its upper side with a circular or rectangular opening 50 around which a flange 52 extends on the outside of the wall. The flange 52 is bolted, welded or otherwise fastened to the wall 26. In the case where the opening 50 is circular, the measuring arrangement 46 is provided with a cylindrical housing 54 that extends in the interior of the flange 52. A further flange 56 is provided on the outside of the housing 54 that is rigidly connected with the housing 54 and lies in contact upon the flange 52. A bolted connection 58 retains the flange 56 of the housing 54 to the flange 52 of the wall 26. In place of a bolted connection 58, any other connection could be selected, preferably a connection that is easily and rapidly connected and disconnected.

An electronic unit 60 is located within the housing 54 at its upper end and contains switching elements for the supply of current for the measuring arrangement 46, for data transmission over a bus system 64 and for evaluation of the measurement results. The electronic unit 60 is connected to the bus system 64 of the harvesting machine 10 over a removable electric plug-in connection 62, to which the on-board computer 40 is also connected. As a rule, the bus system 64 operates according to a standard such as CAN ISO 11783. The measuring arrangement 46 announces its presence to the display arrangement 38 with its own site or alternatively only with values that are displayed on another site.

Furthermore, a light source 66 is located within the housing 54 and radiates light downward by means of a collimator 68. The light travels through a pane 70, that is transparent to light, located on the underside of the housing 54, and travels into the conveying channel 72 in the discharge duct 26, through which harvested crop 74 is conveyed. Light reflected by the harvested crop 74 falls upon detectors 76, that are shielded from the light source 66 by a non-transparent barrel 78. The detectors 76 are able to detect the reflectivity of the harvested crop 74 in specific wave lengths, that is, they are configured as spectrometers. For this purpose, filters, grating, or dispersive elements can be used that are known in themselves. The electronic unit 60 calculates the contents of certain specific components such as moisture, starch, enzyme soluble organic components, inorganic mineral components, raw protein, oil and the like. The measured values are transmitted to the on-board computer 40 over the bus system 64. The computer 40 maps the data as a function of their location and transmits the data to the display arrangement 38, where they can be displayed.

The flange 52 and the bolted connection 58 together with the plug-in connection 62 form a first retaining arrangement 80, for the measuring arrangement 46, which can be disconnected. After releasing the bolted connection 58, the measuring arrangement 46 can be removed from the discharge duct 26 without any further steps. If the harvesting machine 10 is to be operated without the measuring arrangement 46, the opening 50 is preferably closed by a blind flange.

As is shown in FIG. 3, the measuring arrangement 46 that was shown in FIGS. 1 and 2, can also be used at any other desired location. In FIG. 3, it is attached to a stationary or portable container 82 which may be a sample container. The portable container 82 is provided with a retaining arrangement 84 at a side wall to which the measuring arrangement 46 is fastened. In its configuration, the retaining arrangement 84 corresponds to the retaining arrangement 80 of FIG. 2. The measuring arrangement 46 is connected by the plug-in connection 62 and a cable 86 and, as a rule, over an appropriate interface, to a computer 88 which is connected, in addition, to a keyboard 90 and a monitor 92.

In this way, the result is that the measuring arrangement 46 can be used during the harvesting operation on the harvesting machine 10, in order to detect the contents of the harvested crop 74 with respect to various components. When not in use, for example, at night, the technically sophisticated and costly measuring arrangement 46 can easily be removed from the harvesting machine 10 in order to store it in a safe place protected against atmospheric influences. In addition it can also be attached to the container 82. Samples stored in the container that consist, for example, of harvested crop of any desired type, can be investigated with the same measuring arrangement 46. The results of the measurement are displayed on the monitor 92 and stored in memory on a memory device in the computer 88. It is also conceivable that the measuring arrangement 46 itself could be provided with an input and a display arrangement, in order to operate it as an individual implement independently of any other implements. The input and monitoring arrangement can be removable and connected to the plug-in connection 62. These can also provide the current supply by means of the electrical network, batteries or the vehicle battery.

In some applications the signals transmitted by the detectors 76 may require differing evaluations depending on which retaining arrangement is used for the measuring arrangement 46. In other words, calibration values of the measuring arrangement depend on its attachment. In order to avoid errors arising from this fact, without having to provide a manual input, in a preferred embodiment of the invention, the electronic unit 60 of the measuring arrangement 46 is provided with information about the retaining arrangement 80 or 84 to which the measuring arrangement 46 is attached at that particular time. This information may consist of data that are transmitted over the bus system 64 or the cable 86. In other embodiments this information is transmitted by means of flanges 52 and is detected by the sensors of the measuring arrangement 46, for example, optically, mechanically or magnetically. Alternatively the measuring arrangement 46 could detect whether it is on the harvesting machine 10 or is used in individual operation (FIG. 3) on the basis of the other devices connected to the bus system 64. The bus system 64 also permits a diagnosis of the measuring arrangement 46.

Moreover the form of the data transmitted by the measuring arrangement 46 can depend on the question whether it is applied on the harvesting machine 10 or is stationary. In that way, differing protocols can be used for data transmission or other data formats could be used. Therefore the information in which form the data are transmitted is, appropriately, a function of the information about the retaining arrangement 80 or 84 to which the measuring arrangement 46 is attached at any given time in the manner described above.

Having described the preferred embodiment, it will become apparent that various modifications can be made without departing from the scope of the invention as defined in the accompanying claims.

The invention claimed is:

1. In combination with a crop harvesting vehicle, a measuring arrangement mounted to said vehicle and arranged to interact with crop material to be investigated in order to detect at least one component of the material, the improvement comprising: said measuring arrangement being fastened to said vehicle by means of a retaining arrangement, so that the measuring arrangement can be operated in the condition in which it is fastened to the retaining arrangement in order to analyze crop material handled and/or processed by said harvesting vehicle, said measuring arrangement having means for readily connecting to and disconnecting from said retaining arrangement thereby permitting said measuring arrangement to be easily separated from said retaining arrangement and used to investigate material in a stationary application.

2. The combination, as defined in claim 1, wherein said measuring arrangement includes an optical sensor that operates in the near infra-red region.

3. The combination, as defined in claim 1, and further including a second retaining arrangement similar in construction to said first-mentioned retaining arrangement and being separated from said harvesting vehicle and associated with a sample container for containing sample material for being measured by said measuring arrangement when the latter is attached to said second retaining arrangement.

4. The combination, as defined in claim 1, wherein said vehicle is provided with a bus system; and said measuring arrangement being connected to said bus system.

5. The combination, as defined in claim 4, wherein measuring arrangement and said bus system including cooperating parts defining a plug-in connection which can be disconnected.

6. The combination, as defined in claim 1, wherein said vehicle is equipped with a display arrangement; and said measuring arrangement being coupled to said display arrangement of the vehicle whereby measurement values can be displayed.

* * * * *